(12) United States Patent
Fredrickson et al.

(10) Patent No.: US 8,097,291 B2
(45) Date of Patent: Jan. 17, 2012

(54) METHODS FOR COATING WORKPIECES

(75) Inventors: Gerald Fredrickson, Westford, MA (US); Lan Pham, Nashua, NH (US); Marlene Schwarz, Auburndale, MA (US); Todd Robida, Southbridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1172 days.

(21) Appl. No.: 11/446,262

(22) Filed: Jun. 5, 2006

(65) Prior Publication Data

US 2007/0281092 A1 Dec. 6, 2007

(51) Int. Cl.
*B05D 3/04* (2006.01)
*B05D 3/14* (2006.01)
*B05D 1/32* (2006.01)

(52) U.S. Cl. ....... 427/2.1; 427/2.24; 427/2.25; 427/458; 427/282

(58) Field of Classification Search .................. 427/458, 427/2.1, 2.24, 2.25
See application file for complete search history.

(56) References Cited

U.S. PATENT DOCUMENTS

| | | | |
|---|---|---|---|
| 5,091,205 A | | 2/1992 | Fan |
| 6,156,373 A * | | 12/2000 | Zhong et al. .................. 427/2.28 |
| 6,322,847 B1 | | 11/2001 | Zhong et al. |
| 6,368,658 B1 | | 4/2002 | Schwarz et al. |
| 6,645,547 B1 | | 11/2003 | Shekalim et al. |
| 6,676,987 B2 | | 1/2004 | Zhong et al. |
| 6,743,463 B2 * | | 6/2004 | Weber et al. .................. 427/2.24 |
| 6,764,709 B2 | | 7/2004 | Flanagan |
| 6,821,549 B2 * | | 11/2004 | Jayaraman .................... 427/2.24 |
| 6,861,088 B2 | | 3/2005 | Weber et al. |
| 6,939,320 B2 | | 9/2005 | Lennox |
| 6,984,411 B2 | | 1/2006 | Palasis et al. |
| 7,390,524 B1 * | | 6/2008 | Chen ............................ 427/2.24 |
| 7,553,377 B1 * | | 6/2009 | Chen et al. ..................... 118/500 |
| 2002/0017503 A1 | | 2/2002 | Banas et al. |
| 2003/0215564 A1 | | 11/2003 | Heller et al. |
| 2004/0185168 A1 * | | 9/2004 | Weber et al. ................... 427/2.1 |
| 2006/0216431 A1 * | | 9/2006 | Kerrigan ....................... 427/458 |

FOREIGN PATENT DOCUMENTS

| | | |
|---|---|---|
| EP | 1325758 | 7/2003 |
| WO | WO00/66189 | 11/2000 |

OTHER PUBLICATIONS

International Preliminary Report on Patentability, including Written Opinion of the International Searching Authority, PCT/US2007/011078, mailed Dec. 24, 2008.
International Search Report and Written Opinion, PCT/US2007/011078, May 27, 2008.
Partial International Search Report in PCT/US2007/011078, dated Nov. 7, 2007.

* cited by examiner

*Primary Examiner* — Timothy Meeks
*Assistant Examiner* — Cachet I Sellman
(74) *Attorney, Agent, or Firm* — Kenyon & Kenyon LLP

(57) ABSTRACT

The present invention is directed to methods, processes, and systems for coating portions of a workpiece as well as to workpieces that have themselves been coated in accord with the invention. Under these methods and processes of the invention, a means to repel may be positioned on a mandrel prior to applying a coating to the workpiece. The means to repel may prevent the coating of a target surface of the workpiece.

11 Claims, 5 Drawing Sheets

METHODS FOR COATING WORKPIECES

TECHNICAL FIELD

The present invention generally relates to partially coated workpieces and methods and systems for partially coating a workpiece with a coating or other treatment. More specifically, the present invention relates to workpieces, such as implantable medical devices, and methods and systems for coating these medical devices, wherein a treatment or other coating is applied to some but not all surfaces of the workpiece during a coating process.

BACKGROUND

Coating workpieces is an often repeated procedure in contemporary manufacturing. Workpieces may be coated by methods that include tumble coating, dip coating, and electrostatic spraying. During each of these procedures coating is applied to the workpiece prior to the workpiece being used for an intended purpose.

When the workpiece is formed partially or completely out of lattice struts or some other open framework, each of the faces of these struts or framework is exposed to the coating and coated during the coating methods listed above. By exposing each face of the workpiece to the coating being applied, each exposed face will be covered during the coating process.

When the workpiece being coated is an implantable medical device, such as a stent, all faces of the struts that comprise the stent are coated when using the coating systems identified above. For example, when dip coating is used, each face of the stent struts will be exposed to the coating. This coating will remain when the stent is removed from the dip and will dry on each face of the struts. Coating may also remain in the spaces between the struts. This phenomenon is sometimes called webbing. Here, not only are the individual struts covered, but some or all of the spaces between the struts are spanned by the coating as well.

BRIEF DESCRIPTION

The present invention is directed to methods, processes, and systems for coating portions of a workpiece as well as to workpieces that have themselves been coated in accord with the invention. Under these methods and processes of the invention, a mandrel having one or more of the various means of repelling coating may be positioned with the workpiece and may be used to prevent coating from remaining on one or more selected target areas of the workpiece. In some embodiments, the workpiece may be an implantable medical device and the coating may include a therapeutic.

Other objects and features of the invention are possible. The following detailed description, which, when taken in conjunction with the annexed drawings, discloses some examples of the invention. Other embodiments, which incorporate some or all of the features as taught herein, are also possible.

BRIEF DESCRIPTION OF THE DRAWINGS

Referring to the drawings, which form a part of this disclosure.

DETAILED DESCRIPTION

The present invention regards methods, systems and apparatus for coating one or more surfaces of a workpiece while not coating other surfaces of the workpiece. In some embodiments this may include coating the outside or side surfaces of the struts of a stent while not coating the inside surfaces of the stent. By coating in this fashion the amount of coating resident on the stent may be reduced. Moreover, if the coating contains a therapeutic, a reduction in coating on the stent may allow the therapeutic to be delivered in a more targeted fashion after the stent is implanted because the therapeutic is resident on faces of the struts of the stent adjacent to the targeted tissue.

This selective coating of a workpiece may be accomplished in accord with embodiments of the present invention by associating a mandrel with a workpiece to be coated and then coating the workpiece. This mandrel may contain one or more means for inhibiting or preventing coating from adhering to selected surfaces of the workpiece. These means to repel may have various configurations including one or more orifices positioned on the mandrel, one or more grooves formed on the mandrel, and one or more electrical conductors supported by the mandrel.

Figure 1A:
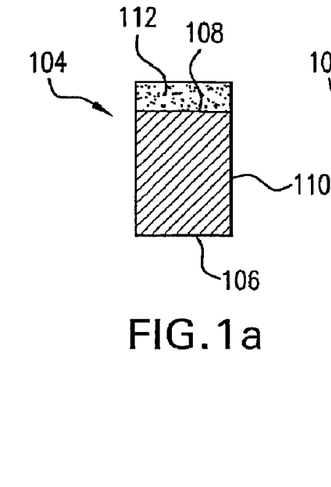
FIG. 1a is a cross-sectional view of a portion of a coated strut from a medical device that has been coated in accord with the present invention.

FIG. 1a is a side sectional view of a strut of a stent that may be coated in accord with the present invention. The strut 104 in FIG. 1a has an inner surface 106, an outer surface 108, and two cut faces 110. Also shown on the strut 104 is a coating 112. As can be seen, the coating 112, covers only one face of the strut 104.

Figure 1B:
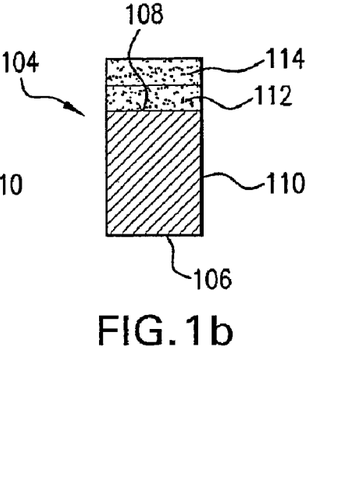
FIG. 1b is a cross-sectional view showing the coated strut of FIG. 1a after a second coating has been applied as may be employed in accord with the present invention.
Figure 1C:
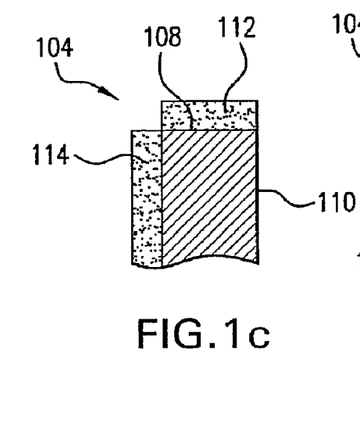
FIG. 1c is a cross-sectional view showing the coated strut of FIG. 1a after a second coating has been applied in accord with the present invention.
Figures 1D, 1E:
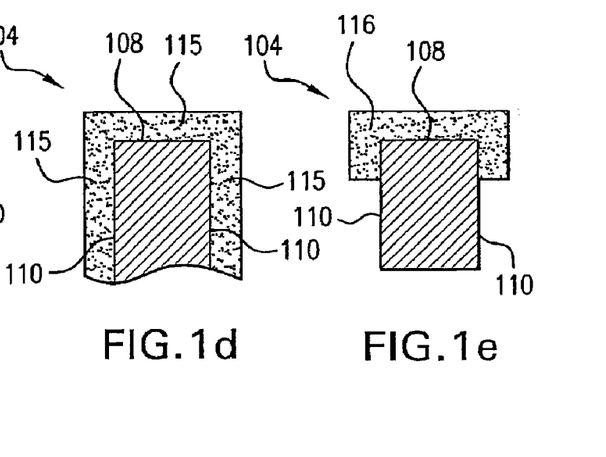
FIG. 1d is another cross-sectional view of a portion of a coated strut from a medical device that has been coated in accord with the present invention.
FIG. 1e is still another cross-sectional view of a portion of a coated strut from a medical device that has been coated in accord with the present invention.

FIG. 1b-1e show examples of how a coating may also be applied in accord with the invention. In FIG. 1b, a first and second coating have been applied to the strut 104. As can be seen, the first coating 112, is in contact with the strut 104 while the second coating 114 is in contact with the first coating 112 and further covers the outer surface 108 of the strut 104. This second coating 114 may be applied in accord with the processes and methods of the present invention. It may also be applied with different methods and processes. In FIG. 1c, the outer surface 108 has been coated with coating 112 while one of the cut faces 110 of the strut 104 has been coated as well; this time with a second coating 114. In FIG. 1d, the outer surface 108 has been coated with coating 115 while both of the cut faces 110 of the strut 104 have been coated as well. In FIG. 1e, the outer surface 108 has been coated with coating 116 while portions of both cut faces 110 of the strut 104 have been coated as well.

In these examples, as well as with the others described herein, if a second coating is employed the coating may comprise the same materials as the first coating or it may differ from the materials used for the first coating. In still other examples, which are not shown, the coating may be applied in other patterns as well. For example, it may be applied to opposing cut faces and not the outer surface 108. In a preferred embodiment, the outer surface 108 is coated one or more times and the two cut faces as well as the inner surface 106 are not coated.

Figure 1F:
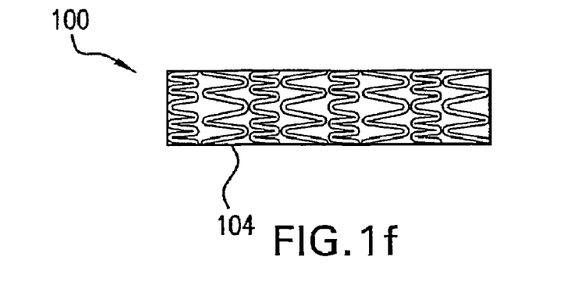
FIG. 1f is a side-view of a coronary stent, which is a medical device that may be coated in accord with the present invention.

FIG. 1f is a side view of an implantable coronary stent that may be coated in accord with the invention. The struts 104 shown in FIGS. 1a-1e are struts that may comprise and make up this stent 100. This stent 100 may be self-expanding, mechanically expandable, or a hybrid stent which may have both self-expanding and mechanically expandable characteristics. The stent 100 may be made in a wide variety of designs and configurations, and may be made from a variety of materials including plastics and metals.

Various methods may be employed for delivery and implantation of the stent 100. For instance, a self-expanding stent may be positioned at the distal end of a catheter around a core lumen. Self-expanding stents may be typically held in an unexpanded state during delivery using a variety of methods including sheaths or sleeves which cover all or a portion of the stent. When the stent is in its desired location of the targeted vessel the sheath or sleeve is retracted to expose the stent which then self-expands upon retraction.

Another method includes mounting a mechanically expandable stent on an expandable member, such as a dilatation balloon provided on the distal end of an intravascular catheter, advancing the catheter through a patient's vasculature to the desired location within the patient's body lumen, and inflating the balloon on the catheter to expand the stent into a permanent expanded condition.

One method of inflating the balloon includes the use of inflation fluid. The expandable member is then deflated and the catheter removed from the body lumen, leaving the stent in the vessel to hold the vessel open.

While the workpiece shown in these initial figures is a stent, many other workpieces may be coated in accord with the invention. For example, other medical devices that may be coated include filters (e.g., vena cava filters), stent grafts, vascular grafts, intraluminal paving systems, implants and other devices used in connection with drug-loaded polymer coatings. Likewise, the workpiece may not be an implantable medical device but may, instead, be another piece that needs to be coated only on certain pre-selected surfaces. In some instances these medical devices or other workpieces may be made from conductive materials and in other instances they may not be. For example, they may be made from polymers or ceramics.

Figure 2A:
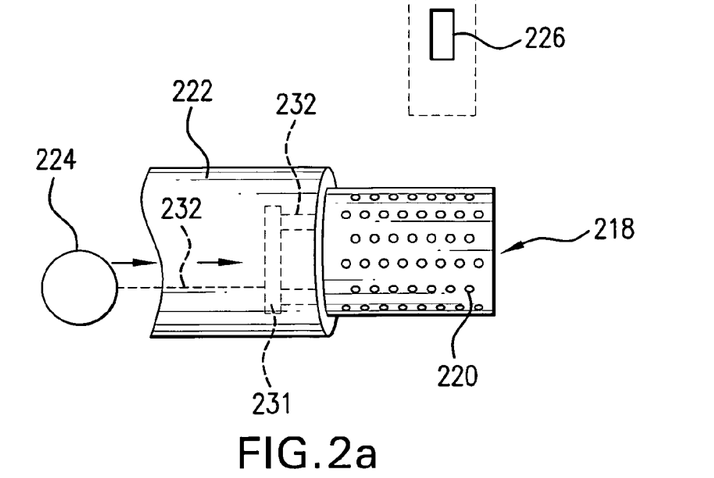
FIG. 2a is a side-view of a mandrel that may be employed in accord with the invention.
Figure 2B:
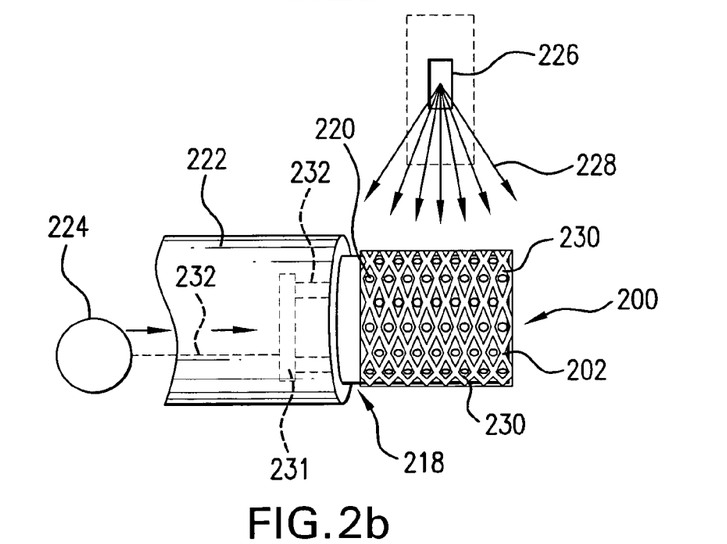
FIG. 2b is the mandrel of FIG. 2a with a workpiece placed over at least a portion of the mandrel.
Figure 2C:
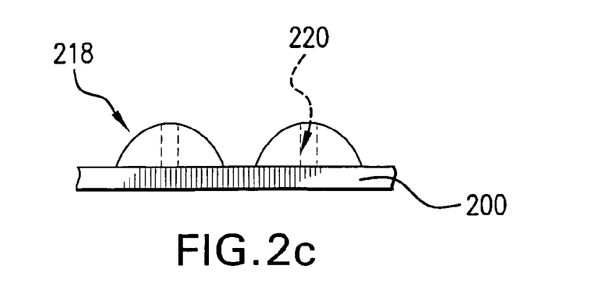
FIG. 2c is a side-view of a resilient portion of the mandrel extending from within the workpiece and through the workpiece.

FIGS. 2a-2c are side-views showing a mandrel 218 including raised apertures 220, a base member 222, a fluid source 224, and a coating sprayer 226 in accord with the embodiments of the invention.

As seen in FIG. 2a, the mandrel 218 may be integrally attached to the base member 222. The mandrel 218 and base member 222 shown are substantially cylindrical, but, any of a variety of shapes and sizes may be used. As can be seen, the raised apertures 220 or means to repel may be provided on an outer surface of the mandrel 218. In some instances the means to repel may comprise only a single raised aperture 220 and in other instances a plurality of raised apertures 220 may be provided.

The mandrel 218 and the base member 222 may be manufactured in some instances from conductive materials and alternatively they may not be. For example, they may be made from a polymeric and/or glass material.

The mandrel 218 and the base member 222 may be insulated in some instances, however, they need not be insulated. For example, it may be preferable to insulate the base member 222 for electrical isolation. Additionally, insulation on the base member 222 may prevent components other than the workpiece 200 from being coated.

Another method of masking the inner surface of the workpiece using electrospray may be to utilize a shrinkable plastic tube, for example, a PTFE tube. Once the workpiece is coated, the shrinkable plastic tube can be thermally treated. This allows for the workpiece to be relatively easily removed without damaging the coating.

FIG. 2c, shows an example where the mandrel 218 is substantially resilient. In the example, the area of the mandrel 218 is larger than that of the workpiece 200. Therefore, portions of the means for repelling on the outer surface of the mandrel 218 extend through the openings 230 of the lattice portion 202. Thus, these protruding portions of the mandrel 218 may repel the coating formulation 228 or inhibit its accumulation on non-target portions of the lattice portion 202. This may be accomplished by the protruding portions of the means for repelling physical interference with the path of the coating. This also may be accomplished by the non-conductive characteristics of the mandrel 218, which repels coating reaching the lattice portion 202.

The workpiece 200 may be fixed, releasably engageable, or moveable with respect to the mandrel 218. For example, in some instances, it may be desirable for the workpiece 200 to rotate freely and/or float with respect to the mandrel 218. Additionally, the mandrel 218 and the workpiece 200 may be positioned so as to selectively contact one another in certain areas.

A fluid source 224 is also illustrated in fluid communication with the means for repelling. As shown, the fluid source 224 can include pneumatic and/or hydraulic components, devices, instruments and systems designed to facilitate or force the flow of fluids such as liquid fluids and those items that use, or are driven by air pressure. The fluid source 224 includes, but is not limited to valves, filters, cylinders, drives, motors, pumps, reservoirs, and tubing.

As can be seen in FIGS. 2*a* and 2*b*, the fluid source 224 communicates with at least one aperture 220 of the means for repelling located on a surface of the mandrel 218. The fluid source 224 may be connected to the apertures via a conduit or conduits 232. In the present example, the conduits fluidly communicate with a manifold 231, however other suitable arrangements may be used For example, although depicted on one side of the mandrel 218, the fluid source 224 can be positioned on any side or surface of the mandrel 218. Furthermore, one or more and any combination of fluid sources 224, manifolds 231, and conduits 232 may be provided. The fluid source 224 may remove from or resist coating of non-target areas of the lattice portion 202. For example, the fluid source 224 may provide air pressure or may draw vacuum. Any suitable fluid can be used. Fluid determination may depend upon the characteristics of coating being applied. For example, suitable fluids for some applications are carbon dioxide ($CO_2$) and nitrogen (N).

In the examples of FIGS. 2*a* and 2*b*, a coating sprayer 226 is illustrated for applying the coating formulation 228. The coating can be applied to the lattice portion 202 by various other methods including, but not limited to, dipping, rolling, spraying, brushing, electrostatic spraying/grafting/plating, spinning, inkjet applications, powdering, vapor deposition, air spraying including atomized spray coating, and spray coating using an ultrasonic nozzle.

One step in a method embodying the invention is to provide a workpiece 200 including a lattice portion 202 and a plurality of openings 230. In FIG. 2*b*, the workpiece 200 is shown positioned on the mandrel 218. The workpiece 200 may be positioned so that openings 230 located on the workpiece align with at least some of the plurality of apertures 220. In the example, the apertures 220 are substantially annular, however, a variety of other shapes and configurations are plausible. For example, slits, slots, projections, recessions, pores, or irregular shaped openings may be used.

In the example of FIG. 2*b*, the fluid source 224 provides pressurized air flow through the apertures 220. The pressurized air may exit the mandrel 218 in a direction towards an inner surface of the workpiece 200. Therefore, in this example, an outward flow of air may be created from the mandrel 218 through the apertures 220 towards the openings 230.

This flow of air may be initiated when some or all of the apertures, and openings are aligned. As the coating formulation 228 is applied, the outward flow of air may substantially prevent the non-target areas from being coated. In this instance, portions of the inner surface 106 (FIG. 1*a*) and/or cut faces 110 (FIG. 1*a*) of the struts may be prevented from being coating. Meanwhile, the target area of the lattice portion 202 may itself be coated. Specifically, in this example, the outer surface 108 (FIG. 1*a*) of the strut can be coated. Other arrangements and configurations are possible.

As stated above, the mandrel 218 may be resilient so that portions of the mandrel 218 can extend through the openings 230 to further prevent coating of non-target surfaces. For example, the inner surface 106 (FIG. 1*a*) and cut faces 110 (FIG. 1*a*) may be prevented from being coated.

Figure 3A:
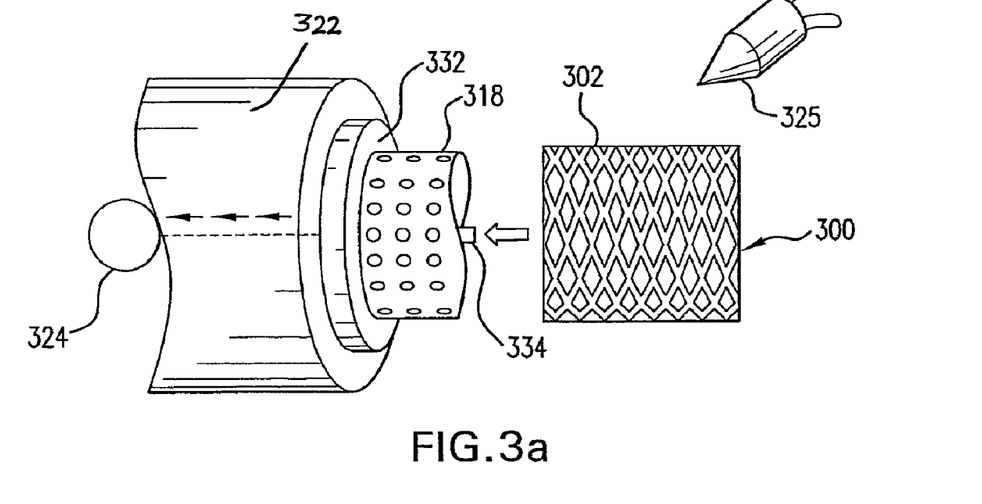
FIG. 3a is a side-view of a mandrel, nozzle, and workpiece before the workpiece is positioned on the mandrel.
Figure 3B:
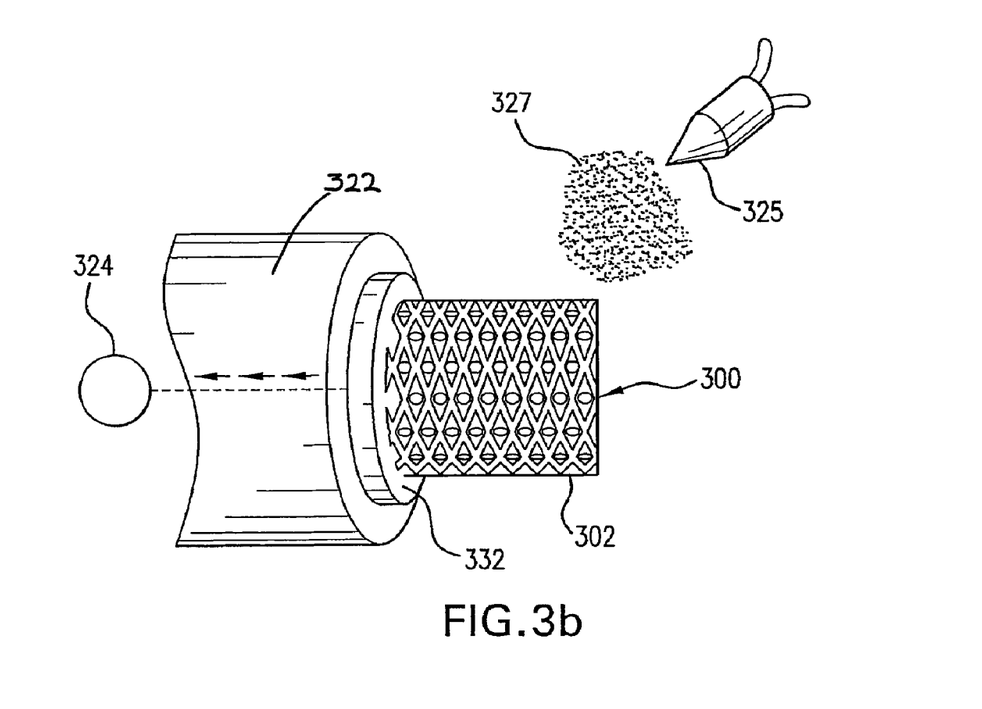
FIG. 3b is a side-view of the mandrel and nozzle from FIG. 3a wherein the workpiece is positioned on the mandrel during electrostatic coating.

FIGS. 3*a* and 3*b* are side-views showing a mandrel 318, nozzle 325, and the workpiece 300 before and after positioning on the mandrel 318 for an electrostatic coating application. Among other coating applications, electro-grafting is also plausible. In order to coat the lattice portion 302 electrostatically, the lattice portion 302, in this case the entire workpiece 300, may be initially grounded or charged by a means to repel. In the example, the lattice portion 302 is charged utilizing a conductor 332 located on the base member 322 of the mandrel 318, the conductor and base member comprising the means to repel; however, the invention is not limited thereto, and any number of alternative grounding or charging configurations can be envisioned. In the example, the base member 322 prevents coating of the conductor 332.

As best seen in FIGS. 3*a* and 3*b*, the lattice portion 302 may be positively charged by the means to repel. In this instance, the coating 327 is also negatively charged. Here, the coating 327 should be attracted only to the targeted surface of the positively charged lattice portion 302. Likewise, the lattice portion 302 may be negatively charged and the coating 327 positively charged.

In this case, since the coating 327 is negatively charged, the coating 327 should be attracted to the outer surface 108 (FIG. 1*a*) and portions of the cut faces 110 (FIG. 1*a*) of the lattice portion 302. Additionally, the inner surface 106 of the lattice portion 302 should be substantially prevented from being coated.

Moreover, in the example, the non-targeted surfaces (e.g. inner surface and cut faces) of each strut 104 (FIG. 1*a*) may be further prevented from coating by positioning a conductive wire 334 on or inside the mandrel 318. In this instance, the conductive wire 334 is positioned inside the mandrel, however, other arrangements are plausible. Also, in the example, the conductive wire 334 may be negatively charged to about the same as the individual drops of negatively charged coating to further prevent coating accumulation on the non-targeted surfaces. If the wire is so charged it is preferred that no surface is in contact with the lumen side of the stent in order to prevent coating and charge from building up within the stent.

Further, as discussed in detail above, a fluid source 324 may also be provided to assist in coating deposit resistance or removal on non-targeted surfaces. In the example, the fluid source 324 draws vacuum on the surface of the mandrel 318 to draw the coating into the mandrel 318 and out through a suitable removal system (not shown).

As stated herein, providing a resilient mandrel 318 may also facilitate prevention of coating of the non-target surfaces. Other modifications, combinations, and alternatives of the above means to repel techniques are possible for the examples of FIGS. 3*a* and 3*b*.

Figure 4A:
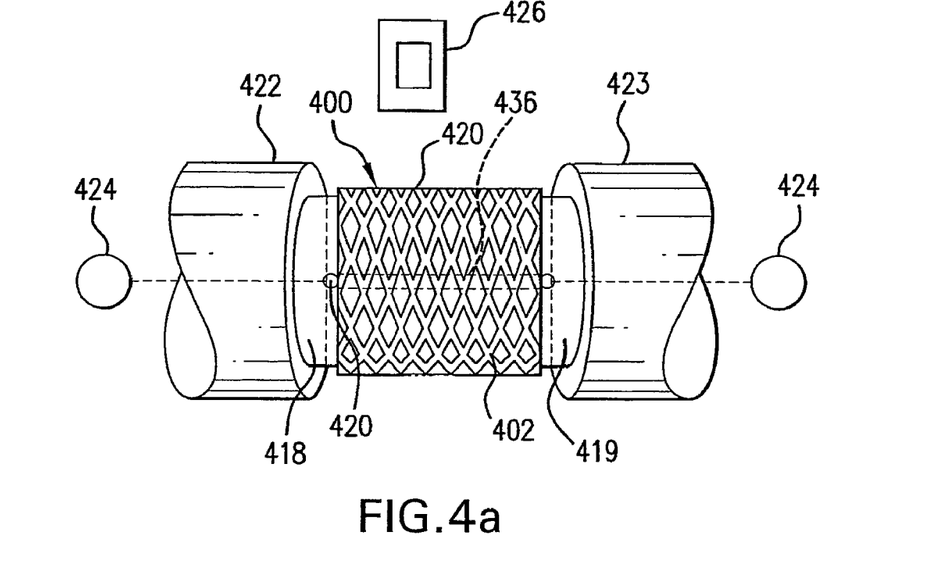
FIG. 4a is a side-view of two mandrels supporting a workpiece as may be employed to coat the workpiece in accord with the invention.
Figure 4B:
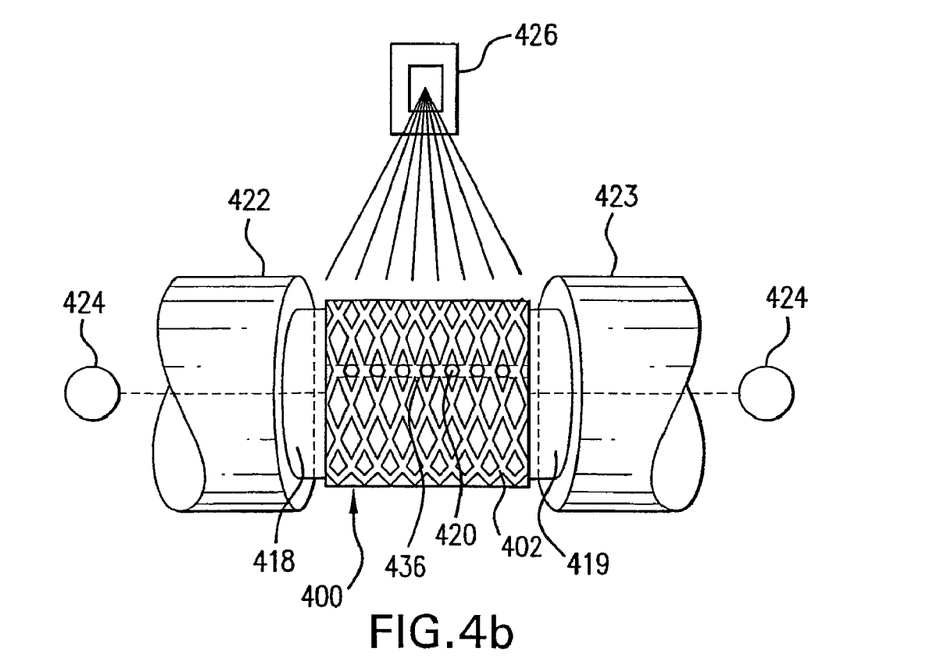
FIG. 4b is a side-view of the two mandrels and workpiece from FIG. 4a showing a coating being sprayed at the workpiece in accord with the invention.

FIGS. 4*a* and 4*b* show a workpiece supported by first and second mandrels 418, 419. The first and second mandrels 418, 419 include first and second base members 422, 423. In this example, the first and second mandrels 418, 419 extend only over a portion of the lattice portion 402, and the center portion of the lattice portion 402 preferably may not contact the mandrels 418, 419. Additionally, in this instance, the first and second mandrels 418, 419 are interconnected by a cross-bar 436, however, other arrangements are possible.

The cross-bar 436 may be substantially cylindrical. The cross-bar 436 may be manufactured in some instances from conductive materials and alternatively it may not be. For example, the cross-bar 436 may be made from a polymeric and/or glass material. As shown in FIGS. 4*a*-*b*, the cross-bar 436 is substantially narrower than the mandrels 418, 419, however, other suitable arrangement may be used. As can be seen, the cross-bar 436 may be provided with one or more apertures 420 to connect the cross-bar with a fluid source.

Each mandrel 418, 419 and cross-bar 436 may be fluidly connected to the fluid source 424. The fluid source 424, facilitates removal from or resistance to coating in non-target areas by providing air pressure or drawing vacuum through apertures 420.

The arrangements illustrated in FIGS. 4a and 4b are merely exemplary, and a number of alternative arrangements using first and second mandrels 418, 419, with or without a crossbar 436, can be envisioned. Additionally, in the example, the workpiece 400 is being spray coated with a coat sprayer 426; however, any suitable coating application processes set forth herein above may be used including roll coating.

Figure 5A:
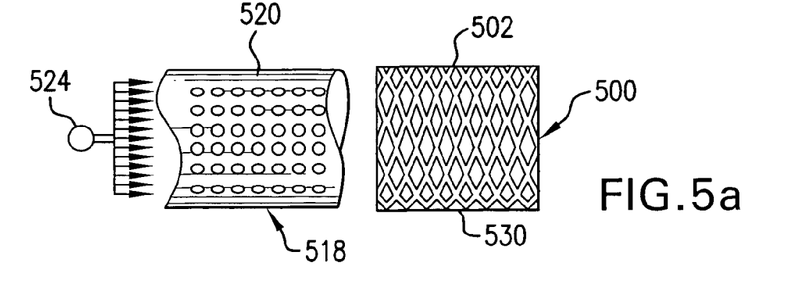
FIG. 5a is a side-view of a mandrel having a plurality of apertures in accord with embodiments of the present invention.
Figure 5B:
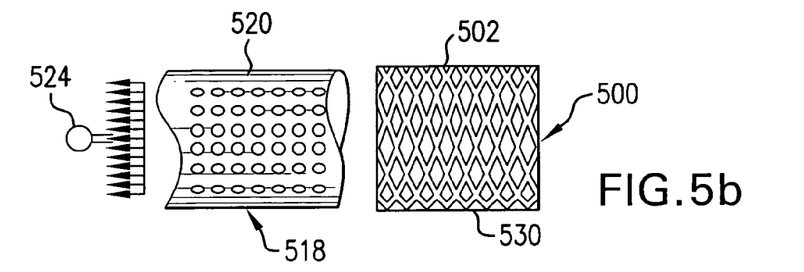
FIG. 5b is a side-view of a mandrel having a plurality of apertures in accord with embodiments of the present invention.

FIGS. 5a-5d illustrate a variety of additional mandrel configurations. As seen in FIG. 5a, a mandrel 518 including a plurality of apertures 520 or means for repelling located on an outside surface is shown. The apertures 520 may be fluidly connected to a fluid source 524 to receive pressurized air therethrough. The pressurized air may resist the formation of coating on non-targeted surfaces of the lattice portion 502. In another example shown in FIG. 5b, a plurality of apertures 520 may be fluidly connected to a fluid source 524 so that a vacuum may be drawn via the apertures 520 to remove coating to prevent coating of non-targeted surfaces of the lattice portion 502.

Figure 5C:
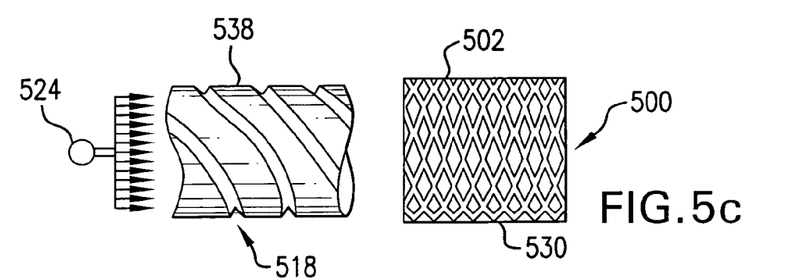
FIG. 5c is a side-view of a mandrel having a plurality of grooves in accord with embodiments of the present invention.

FIG. 5c illustrates a mandrel 518 having a plurality of grooves 538. In this instance, the grooves 538 or means for repelling are spiral shaped and in connection with a fluid source 524. The grooves 538 may be any shape and may be configured so as to provide an air stream. The air stream may travel through the grooves 538 and may impart rotation to the workpiece 500 with respect to the mandrel 518. Such a configuration may enable the mandrel 518 to act as an internal air knife to remove excess coating. Rotation of the mandrel 518 may also allow gravity to facilitate removal of excess coating which may result in improved uniformity of the coating.

Other types and shapes of groove 538 arrangements are possible in accord with embodiments of the present invention.

Figure 5D:
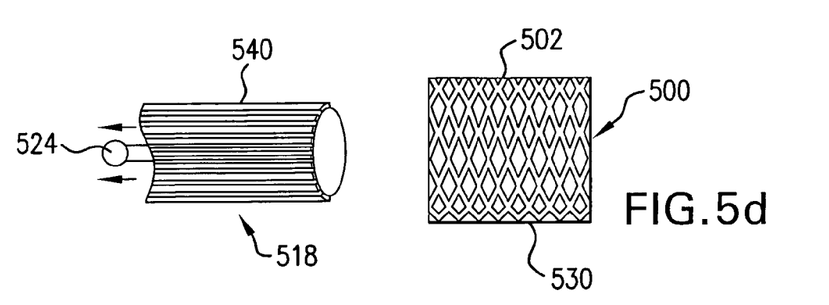
FIG. 5d is a side-view of a mandrel having a plurality of protrusions in accord with embodiments of the present invention.

In still yet another example, FIG. 5d illustrates a substantially cylindrical mandrel 518 including a plurality of protrusions 540 or means for repelling located on an outer surface thereof. In the example, the protrusions 540 or means for repelling are pins, however, other arrangements and configurations are plausible. In this instance, the protrusions 540 are positioned in a series of rows disposed parallel to one another. The protrusions extend in a direction substantially perpendicular to a surface of the mandrel 518. In the example, the protrusions 540 may elevate portions of the workpiece 500 from a surface of the mandrel 518. The protrusions 540 may also provide a space to trap excess coating and prevent the coating from accumulating in the lattice portion 502.

Figure 5E:
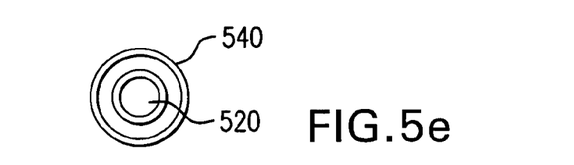
FIG. 5e is a top-view of one of the plurality of protrusions from the mandrel of FIG. 5d in accord with embodiments of the present invention.

FIG. 5e is a top view of one of the protrusions 540 from the mandrel 518 of FIG. 5d showing a fluid communication aperture 520. The protrusions 540 can be provided with apertures 520 to fluidly communicate the protrusions 540 with a fluid source 524. Via the apertures 520, air pressure or vacuum can be provided or drawn to/from a surface of the mandrel 518. It is also plausible that the protrusions 540 may also extend through the openings 530 to physically prevent accumulation of the coating.

While various embodiments have been described, other embodiments are plausible. For example, in certain instances the fluid can be heated or cooled if desired to assist in the repelling of coating from non-targeted surfaces.

It should be understood that the foregoing descriptions of various examples of the mandrel are not intended to be limiting, and any number of modifications and combinations of the examples may be employed within the spirit and scope of the present invention.

The coating, in accord with the embodiments of the present invention, may comprise a polymeric and or therapeutic agent formed, for example, by admixing a drug agent with a liquid polymer, in the absence of a solvent, to form a liquid polymer/drug agent mixture. A suitable list of drugs and/or polymer combinations is listed below. The term "therapeutic agent" as used herein includes one or more "therapeutic agents" or "drugs". The terms "therapeutic agents" or "drugs" can be used interchangeably herein and include pharmaceutically active compounds, nucleic acids with and without carrier vectors such as lipids, compacting agents (such as histones), viruses (such as adenovirus, andenoassociated virus, retrovirus, lentivirus and α-virus), polymers, hyaluronic acid, proteins, cells and the like, with or without targeting sequences.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; anti-proliferative agents such as enoxaprin, angiopeptin, rapamycin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/anti-proliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents;

agents which interfere with endogenous vasoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMPs"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMPs are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them.

As stated above, coatings used with the exemplary embodiments of the present invention may comprise a polymeric material/drug agent matrix formed, for example, by admixing a drug agent with a liquid polymer, in the absence of a solvent, to form a liquid polymer/drug agent mixture. Curing of the mixture typically occurs in-situ. To facilitate curing, a cross-linking or curing agent may be added to the mixture prior to application thereof. Addition of the cross-linking or curing agent to the polymer/drug agent liquid mixture must not occur too far in advance of the application of the mixture in order to avoid over-curing of the mixture prior to application thereof. Curing may also occur in-situ by exposing the polymer/drug agent mixture, after application to the luminal surface, to radiation such as ultraviolet radiation or laser light, heat, or by contact with metabolic fluids such as water at the site where the mixture has been applied to the luminal surface. In coating systems employed in conjunction with the present invention, the polymeric material may be either bioabsorbable or biostable. Any of the polymers described herein that may be formulated as a liquid may be used to form the polymer/drug agent mixture.

The polymer used in the exemplary embodiments of the present invention is preferably capable of absorbing a substantial amount of drug solution. When applied as a coating on a medical device in accordance with the present invention, the dry polymer is typically on the order of from about 1 to about 50 microns thick. In the case of a balloon catheter, the thickness is preferably about 1 to 10 microns thick, and more preferably about 2 to 5 microns. Very thin polymer coatings, e.g., of about 0.2-0.3 microns and much thicker coatings, e.g., more than 100 microns, are also possible. It is also within the scope of the present invention to apply multiple layers of polymer coating onto a medical device. Such multiple layers are of the same or different polymer materials.

The polymer of the present invention may be hydrophilic or hydrophobic, and may be selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHYDROL®, etc.) and acrylic latex dispersions are also within the scope of the present invention. The polymer may be a protein polymer, fibrin, collagen and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment of the invention, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference. U.S. Pat. No. 5,091,205 describes medical devices coated with one or more polyisocyanates such that the devices become instantly lubricious when exposed to body fluids. In another preferred embodiment of the invention, the polymer is a copolymer of polylactic acid and polycaprolactone.

The examples described herein are merely illustrative, as numerous other embodiments may be implemented without departing from the spirit and scope of the exemplary embodiments of the present invention. Moreover, while certain features of the invention may be shown on only certain embodiments or configurations, these features may be exchanged, added, and removed from and between the various embodiments or configurations while remaining within the scope of the invention. Likewise, methods described and disclosed may also be performed in various sequences, with some or all of the disclosed steps being performed in a different order than described while still remaining within the spirit and scope of the present invention.

What is claimed is:

1. A method of coating a surface of a workpiece, the method comprising:
   providing a workpiece including a lattice portion, the lattice portion having a plurality of struts;
   providing a mandrel to support the workpiece, the mandrel including means to prevent coating adherence, wherein the means to prevent coating adherence fluidly connects a surface of the mandrel with a fluid source;
   applying an electrically charged coating to a target surface of the lattice portion while the means to prevent coating adherence acts to prevent the coating from adhering to selected areas of the workpiece;
   providing a conductor that contacts the lattice portion to ground or electrically charge the lattice portion, and
   positioning a conductive member on the mandrel and electrically charging the conductive member,
   wherein the coating and the conductive member have like charges.

2. The method of claim 1, wherein the mandrel includes a base member.

3. The method of claim 2, wherein the base member is insulated.

4. The method of claim 2, wherein the conductor is located on the base member.

5. The method of claim 1, wherein the fluid source is a vacuum source which draws the coating into the mandrel.

6. The method of claim 1, wherein the mandrel is resilient so that at least a portion of the mandrel extends through an opening of the lattice portion to prevent the coating from adhering to non-target surfaces.

7. The method of claim 1, wherein the conductive member is a wire.

8. A method of coating a surface of a workpiece, the method comprising:
   providing a workpiece including a lattice portion, the lattice portion having a plurality of struts;
   providing a mandrel to support the workpiece, the mandrel including means to prevent coating adherence, wherein the means to prevent coating adherence fluidly connects a surface of the mandrel with a fluid source; and
   applying a coating to a target surface of the lattice portion while the means to prevent coating adherence acts to prevent coating from adhering to selected areas of the workpiece,
   wherein the mandrel is inflatable.

9. A method of coating a surface of a workpiece, the method comprising:
   providing a workpiece including a lattice portion, the lattice portion having a plurality of struts;
   providing a first mandrel to support the workpiece, the mandrel including means to prevent coating adherence;
   providing a second mandrel to support the workpiece; and
   applying a coating to a target surface of the lattice portion while the means to prevent coating adherence acts to prevent coating from adhering to selected areas of the workpiece,
   wherein a cross-bar extends between the first and second mandrels.

10. The method of claim 9, wherein the means to prevent coating adherence fluidly connects at least one surface of one of the mandrels or the cross-bar with a fluid source.

11. The method of claim 10, wherein the means to prevent coating adherence includes at least one aperture.

* * * * *